United States Patent [19]

Grabenkort

[11] Patent Number: 5,775,506
[45] Date of Patent: Jul. 7, 1998

[54] PHARMACEUTICAL AMPUL

[75] Inventor: Richard W. Grabenkort, Barrington, Ill.

[73] Assignee: Abbott Laboratories, Abbott Park, Ill.

[21] Appl. No.: 719,744

[22] Filed: Sep. 25, 1996

[51] Int. Cl.[6] .................................................. B65D 85/00
[52] U.S. Cl. .................... 206/571; 206/438; 215/DIG. 3; 604/232
[58] Field of Search .................... 206/571, 570, 206/438, 219, 222; 215/DIG. 3, DIG. 8; 604/200, 232–235, 257

[56]  References Cited

U.S. PATENT DOCUMENTS

| | | |
|---|---|---|
| 1,718,603 | 6/1929 | Smith ................................ 604/232 |
| 2,706,479 | 4/1955 | Lockhart ........................... 604/232 |
| 2,847,011 | 8/1958 | Jones ................................. 604/232 |

*Primary Examiner*—Jimmy G. Foster
*Attorney, Agent, or Firm*—Brian R. Woodworth

[57]  ABSTRACT

A pharmaceutical container having a body defining a chamber therein. The body includes a first end portion and a second end portion. A terminal end is included on the second end portion. A plug is positioned in the chamber defined by the body such that the plug is spaced from the terminal end. The plug and the body define a first chamber portion of the chamber between the plug and the first end portion of the body. The plug and the body define a second chamber portion of the chamber between the plug and the terminal end of the second end portion. The plug substantially fluidly seals the second chamber portion from the first chamber portion. The body is frangible at a position on the second end portion between the plug and the terminal end.

10 Claims, 2 Drawing Sheets

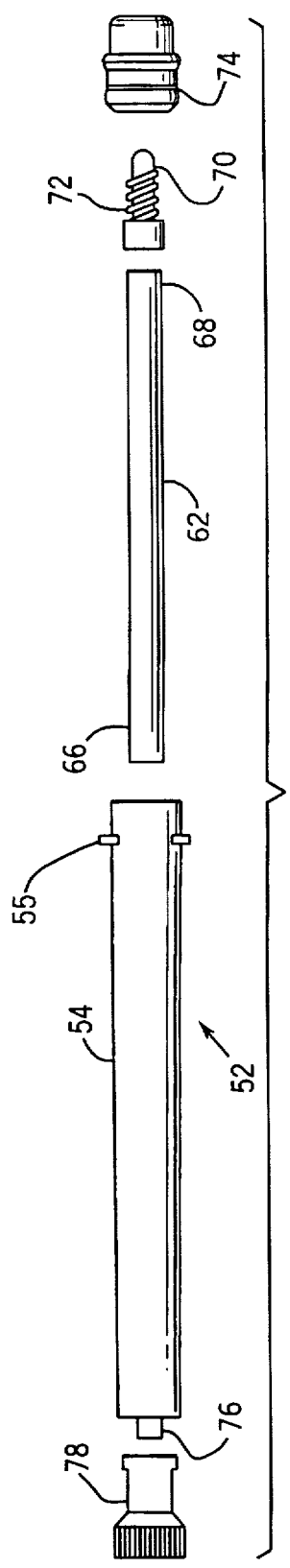
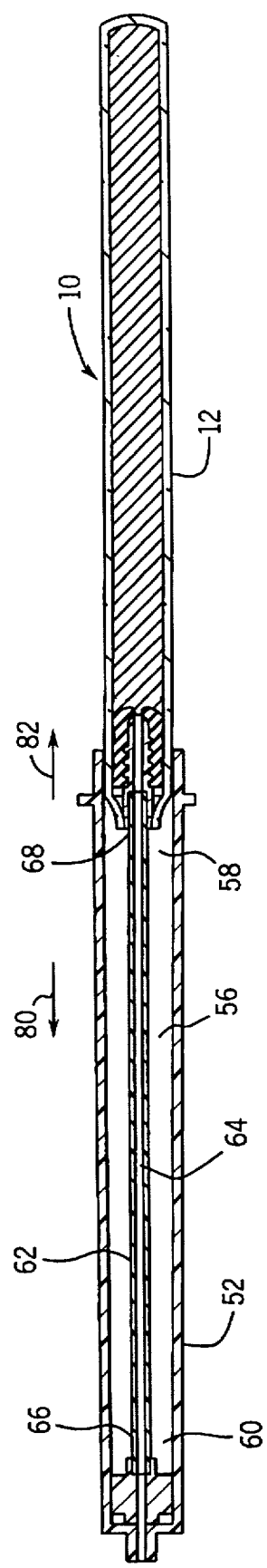

PHARMACEUTICAL AMPUL

TECHNICAL FIELD

This invention relates to an ampul for containing a pharmaceutical product. In particular, the present invention is directed to an ampul having a frangible portion where the frangible portion is separated from the pharmaceutical product by a plug.

BACKGROUND OF THE INVENTION

Pharmaceutical products can be delivered in a variety of different containers, including vials, pre-filled syringes, and ampuls. Ampuls are typically provided in the form of a tube that is sealed upon itself at both ends, thereby providing a fluid-tight container without the need for an additional closure device such as a stopper. In order to gain access to the contents of an ampul, it is necessary to break off a portion of the tube. Shards of material from the tube may be dispersed as a result of the breaking of the tube. These shards may be released into the pharmaceutical product contained in the ampul, thereby necessitating the filtering of the pharmaceutical product prior to its delivery to a patient. It therefore is desirable to provide an ampul that reduces the likelihood that such shards will be released into the pharmaceutical product contained in the ampul.

SUMMARY OF THE INVENTION

The ampul of the present invention includes a body defining a chamber therein. The body includes a first end portion, a second end portion, and a terminal end on the second end portion. A plug is positioned within the chamber at a point spaced from the terminal end to define a first chamber between the plug and the first end portion of the body and a second chamber between the plug and the terminal end of the body. The plug substantially isolates the first chamber from the second chamber. The body is frangible at a point on the second end portion between the plug and the terminal end.

The present invention also is directed to a method for packaging a pharmaceutical product that includes the step of providing a container defining a chamber therein. The container includes a first end portion, a second end portion, and a terminal end on the second end portion, the first end portion being open to an external environment of the container. The container is frangible at a point on the second end portion. The method further includes the step of providing a plug constructed to be slidable within the chamber. The plug is placed into the chamber defined by the container at a position on the first end portion side of the point at which the container is frangible so as to define a first chamber and a second chamber. A pharmaceutical product is provided and a quantity of such product is placed into the first chamber portion. The first end portion of the container is then fluidly sealed.

The present invention also is directed to a system for delivering a pharmaceutical product. The system includes a container body defining a chamber therein. The container includes a first end portion, a second end portion, and a terminal end on the second end portion. A plug is positioned in the chamber such that the plug is spaced from the terminal end. The plug and the first end portion of the body define a first chamber and the plug and the second end portion of the body define a second chamber. The container body is frangible at a position on the second end portion between the plug and the terminal end. The system further includes a syringe having a body defining a chamber therein, the chamber being constructed to receive therein the body of the pharmaceutical container. The syringe body has a first end that is open and a second end opposite the first end. The syringe also includes a fluid flow member mounted within the chamber defined by the syringe body. A fluid flow channel is defined through the fluid flow member from a first end portion to a second end portion thereof. A means for establishing fluid contact between the first chamber of the container and the fluid flow channel is provided on the first end portion of the fluid flow member. A means for establishing fluid communication between the fluid flow channel and an external environment is provided on the second end portion of the fluid flow member.

BRIEF DESCRIPTION OF THE DRAWINGS

In the accompanying drawings that form part of the specification:

FIG. 5 is an exploded view of a syringe constructed in accordance with the present invention; and FIG. 6 is cross-sectional view of the preferred embodiment of the ampul of the present invention in combination with the syringe of the present invention.

DESCRIPTION OF THE PREFERRED EMBODIMENT

While this invention is susceptible of embodiment in many different forms, this specification and the accompanying drawings disclose only one specific form as an example of the invention. The invention is not intended to be limited to the embodiment so described. The scope of the invention is set forth in the appended claims.

The figures illustrating the apparatus show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

The apparatus of this invention is used with certain conventional components the details of which, although not fully illustrated or described, will be apparent to those having skill in the art and an understanding of the necessary functions of such components.

Figure 2:
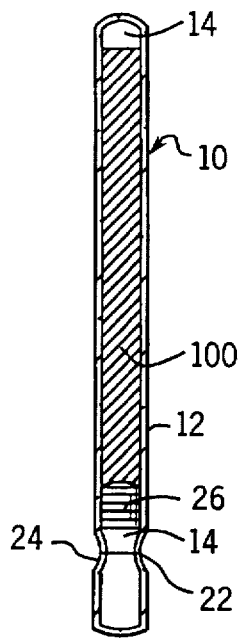
FIG. 2 is a cross-sectional view of an alternative embodiment of the ampul of the present invention after closure of the first end portion of the body of the ampul.

A pharmaceutical ampul constructed in accordance with the present invention is depicted at 10 in FIG. 2. Ampul 10 includes body 12 which defines chamber 14 therein. Ampul 10 also includes first end portion 16 and second end portion 18. Second end portion 18 includes terminal end 20 which is closed, i.e., terminal end 20 encloses chamber 14 from an external environment thereof. Although body 12 is depicted in the accompanying figures as having a substantially tubular configuration, it will be appreciated by one of ordinary skill in the art that other configurations of body 12 are possible without departing from the spirit and scope of the present invention. Body 12 can be constructed of a variety of known materials, including polymeric materials and glass. In the embodiment of the present invention, body 12 is constructed of glass.

Second end portion 18 is constructed to be frangible at one or more points 22 along its length. In the preferred embodiment of the present invention depicted in the accompanying figures, second end portion 18 includes necked-in portion 24. In the preferred embodiment, body 12 is rendered frangible at frangible point 22 which is positioned along necked-in portion 24. Placement of frangible point 22 along necked-in portion 24 will serve to identify to a user the location of frangible point 22, thereby facilitating the opening of ampul 10. It will be appreciated that a variety of known methods for rendering second end portion 18 frangible can be used and that the preferred method is dependent upon the material used to construct body 12.

Figure 1:
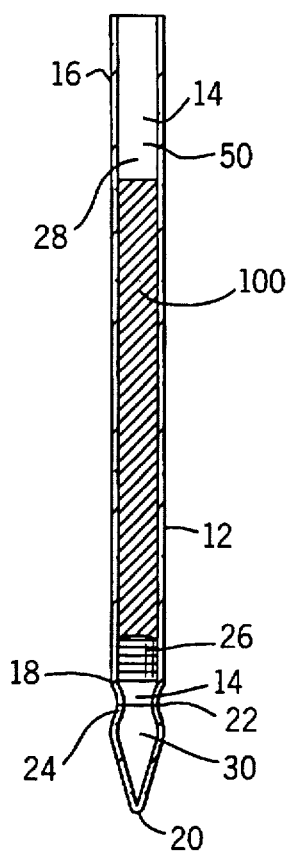
FIG. 1 is cross-sectional view of the ampul of the present invention prior to closure of the first end portion of the body of the ampul.
Figure 3:
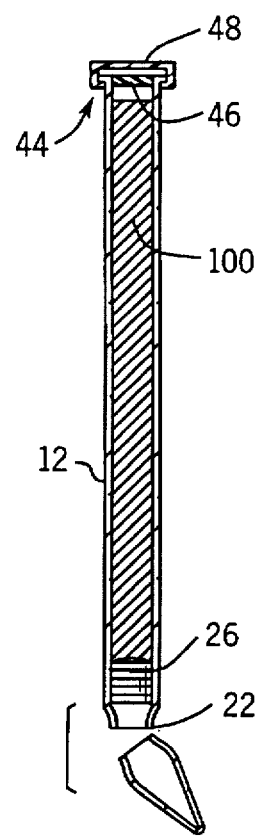
FIG. 3 is a cross-sectional view of the ampul of the present invention after the second end portion of the body of the ampul has been broken.

As depicted in FIGS. 1 and 3, terminal end 20 of body 12 can be substantially pointed. This configuration of terminal end 20 is representative of most ampuls currently used in the medical industry. It will be appreciated that the present invention is not limited to this configuration of terminal end 20. For example, it may be desirable to configure terminal end 20 such that it is substantially flat, as depicted in FIG. 2, thereby facilitating the manufacture, transport, and filling of body 12. One of ordinary skill in the art will appreciate that other configurations of terminal end 20 are possible without departing from the spirit and scope of the present invention.

Plug 26 is disposed within chamber 14 on the first end portion side of frangible point 22, as depicted in the accompanying figures. In the preferred embodiment of plug 26 of the present invention depicted in FIG. 4, plug 26 is contoured along exterior surface 102. Contoured exterior surface 102 includes enlarged portions 104 and narrowed portions 106. Enlarged portions 104 have a diameter greater than the diameter of chamber 14 and are therefore compressed when plug 26 is disposed within chamber 14. Narrowed portions 106 have a diameter that is less than or equal to the diameter of chamber 14 and therefore are not compressed when plug 26 is disposed within chamber 14. The functional characteristics and advantages of contoured exterior surface 102 will be described in greater detail herein.

In the preferred embodiment, plug 26 defines first and second chambers 28, 30 within chamber 14. Plug 26 is preferably constructed of an elastomeric material in order to create a substantially fluid-tight seal between plug 26 and body 12. In the preferred embodiment of the present invention, plug 26 is constructed to be slidable through chamber 14, as discussed in detail herein. Pharmaceutical product 100 can be fluidly retained in first chamber 28.

Figure 4:
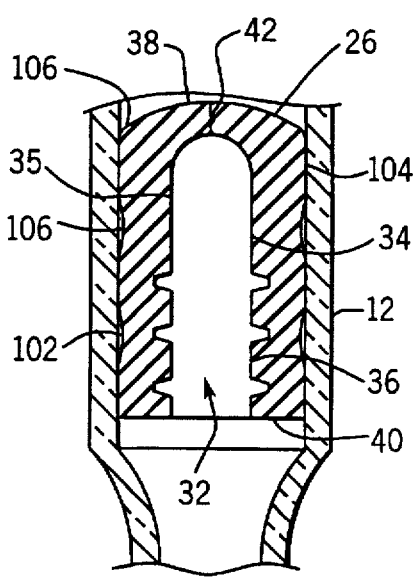
FIG. 4 is an enlarged, elevational view of a plug constructed in accordance with one embodiment of the present invention superimposed on a portion of the ampul of the present invention.

In the preferred embodiment of plug 26 of the present invention depicted in FIG. 4, plug 26 defines channel 32 therethrough. In this embodiment of the present invention, channel 32 includes threadable wall portion 34 having threads 36 formed thereon. Channel 32 of this embodiment further includes pre-pierced channel 42 extending from threadable wall portion 34 through first end 38 of plug 26. Channel 32 thereby extends from second end 40 of plug 26 to first end 38 of plug 26. In this embodiment, pre-pierced channel 42 is configured such that it provides a substantially fluid-tight seal prior to insertion and threaded engagement of a fluid flow member, such as that depicted in FIG. 5, into channel 32. That is, plug 26 preferably substantially inhibits the movement of pharmaceutical product 100 between first chamber 28 and second chamber 30. However, it will be appreciated that some movement of pharmaceutical product 100 between first and second chambers 28, 30 will occur in this embodiment of plug 26 of the present invention, such movement being discussed in detail herein. In addition, surface 35 of pre-pierced channel 42 is configured such that it provides a substantially fluid-tight seal with an exterior surface of a piercing member positioned therein, thereby substantially limiting movement of fluid from first chamber 28 to movement through the piercing member inserted therein, and thereby preventing leakage during transfer of pharmaceutical product 100 from first chamber 28.

In a second embodiment of the present invention not depicted herein, channel 32 includes only pre-pierced channel 42 which extends from first end 38 to second end 40 of plug 26 and threadable portion 34 is omitted. In this embodiment, as is the case with the preferred embodiment of the present invention depicted in FIG. 4, pre-pierced channel 42 is configured such that it provides a substantially fluid-tight seal about a piercing member inserted therein, thereby preventing leakage during the withdrawal of pharmaceutical product from first chamber 28.

In a third embodiment of the present invention not depicted herein, plug 26 does not include a plug channel 32 or a pre-pierced channel 42. In this embodiment, plug 26 is constructed of a material that can be pierced by a cannula or needle of known construction.

First end portion 16 of body 12 is sealed from an external environment of ampul 10 after pharmaceutical product 100 has been placed in first chamber 28. Sealing of first end portion 16 can be effected by conventional heat-sealing methods which cause first end portion 16 to be fluidly sealed upon itself, thereby providing a unitary, sealed body 12, as depicted in FIG. 2. In an alternative embodiment depicted in FIG. 3, first chamber 28 is sealed by placing a sealing member 44 therein. As depicted in FIG. 3, sealing member 44 includes stopper 46 and ferrule 48. Stopper 46 preferably is constructed to provide a substantially fluid-tight seal of first chamber 28. Ferrule 48 is positioned about stopper 46 and is attached to body 12 by conventional methods in order to ensure that stopper 46 is not inadvertently removed from first end portion 16 of body 12. Ferrule 48 can be annular in configuration, but preferably is disc-shaped such that it substantially covers the surface of stopper 46 that is exposed when stopper 46 is positioned in first chamber 28, thereby providing protection for stopper 46. Ferrule 48 preferably is constructed of a malleable polymeric or metal material. Ferrule 48 and stopper 46 preferably are constructed to provide evidence of tampering. One of ordinary skill in the art will appreciate that other configurations of sealing member 44 are possible without departing from the spirit and scope of the present invention.

The manufacturing and filling method of the present invention includes the step of providing a pharmaceutical container such as ampul 10 described in detail herein. First end portion 16 of body 12 is open to an external environment of ampul 10 when the pharmaceutical container is provided in accordance with the method of the present invention. Terminal end 20 of body 12 can be either open or closed to an external environment of ampul 10 when the pharmaceutical container is provided.

The method further includes the step of providing a plug such as plug 26 described in detail herein. Plug 26 is placed into chamber 14 defined by body 12 at a position on the first end portion side of frangible point 22, thereby defining a first chamber 28 between first end 38 of plug 26 and first end portion 16 of body 12 and a second chamber 30 between second end 40 of plug 26 and second end portion 18 of body 12. In the preferred embodiment of the method of the present invention, plug 26 is placed in chamber 14 through first end portion 16 and is urged to its position on the first end portion side of frangible point 22. It will be appreciated that the position of plug 26 will be selected based upon a variety of considerations, including the desired volume of pharmaceutical product 100 to be contained by first chamber 28 of ampul 100. In the event that terminal end 20 of body 12 is open when the pharmaceutical container is provided, plug 26 can be inserted through terminal end 20 and urged into its position on the first end portion side of frangible point 22. It also will be appreciated that the pharmaceutical container can be provided with plug 26 disposed therein, thereby eliminating the need for plug 26 to be placed in chamber 14 of body 12.

Following placement of plug 26 in chamber 14, a pharmaceutical product 100 is provided and a predetermined volume of such product is placed in first chamber 28, as depicted in FIG. 1.

After pharmaceutical product 100 is placed in first chamber 28, first end portion 16 of body 12 is substantially fluidly sealed using known techniques. For example, flame closing can be used to seal first end portion 16 upon itself. If flame closing is used, it may be desirable to provide head space 50 between pharmaceutical product 100 and the point at which first end portion 16 is sealed upon itself, thereby protecting pharmaceutical product 100 from the potentially damaging effects of the heat generated by the flame closing process. In the alternative, a sealing member such as sealing member 44 can be provided and positioned within first end portion 16 of body 12 in order to effect the desired seal. If terminal end 20 of body 12 is not closed when the ampul is provided, it is preferably sealed at this juncture using known techniques such as flame closing.

Ampul 10 of the present invention can be utilized in an aseptic filling process, in which case no additional sterilization of ampul 10 and pharmaceutical product 100 is required following the closure of body 12. However, in the event that an aseptic filling technique is not used, it is preferable that ampul 10 and pharmaceutical product 100 contained therein be subjected to terminal sterilization using known techniques. If heat sterilization is used to terminally sterilize ampul 10 and pharmaceutical product 100, it will be appreciated that pharmaceutical product 100 will produce vapor, some of which will pass through pre-pierced channel 42 and into second chamber 30. This vapor will sterilize second chamber 30. In the event that plug 26 does not include pre-pierced channel 42, it is preferable that a relatively small volume of fluid, e.g., sterile water, be placed in second chamber 30 during the manufacturing and filling procedure such that this volume of fluid will vaporize and sterilize second chamber 30 during terminal sterilization. Other techniques of terminal sterilization can be used in connection with the present invention, including irradiation and light sterilization techniques.

The present invention further includes a system for delivering a pharmaceutical product. The system of the present invention includes, in combination, ampul 10 and syringe 52. Syringe 52, as depicted in FIG. 5, includes syringe body 54 which is configured to receive body 12 therein. Syringe body 54 preferably is configured such that body 12 can be sidably moved into and out of chamber 56 defined by syringe body 54. Syringe body 54 includes first end portion 58 and second end portion 60. First end portion 58 is open to an external environment of syringe 52 such that body 12 can be inserted therein. Gripping flange member 55 is positioned on an external surface of syringe body 54 as depicted in FIG. 5 in order to facilitate use of the system of the present invention.

Second end portion 66 of fluid flow member 62 is mounted on second end portion 60 of syringe 52. Fluid flow member 62 extends through chamber 56 defined by syringe body 54 as depicted in FIG. 6. As depicted, fluid flow member 62 of the preferred embodiment is positioned substantially coaxially with syringe body 54. However, it will be appreciated that fluid flow member 62 need not be coaxial with syringe body 54 in order to function in accordance with the present invention. Fluid flow member 62 defines fluid flow channel 64 therethrough. A plug piercing member 70 is mounted on first end portion 68 of fluid flow member 62. Plug piercing member 70 is constructed to establish fluid flow between first chamber 28 of ampul 10 and channel 64 of fluid flow member 62.

In one embodiment of the present invention, plug piercing member 70 is a cannula constructed to pierce a pierceable stopper. In a second embodiment of the present invention, plug piercing member 70 is a cannula constructed to be inserted through a pre-pierced stopper. In each of these embodiments plug piercing member 70 and stopper 26 are constructed such that a substantially fluid-tight seal is created therebetween, thereby ensuring that pharmaceutical product 100 passes from first chamber 28 into channel 64 of fluid flow member 62 and thereby reducing leakage of pharmaceutical product 100 from ampul 10.

In the embodiment of the present invention depicted in FIG. 5, plug piercing member 70 defines threads 72 thereon which are configured to mate with threads 36 formed on threadable wall portion 34 of plug 26. In this embodiment, plug piercing member 70 is constructed such that it can be threadably secured to threads 36 of plug 26. Plug piercing member 70 also is constructed to provide a substantially fluid-tight seal with surface 35 of plug 26, thereby reducing leakage of pharmaceutical product 100 from ampul 10 when plug piercing member 70 is inserted into plug 26. Further, plug piercing member 70 is constructed such that it causes pre-pierced channel 42 to open as plug piercing member 70 is threadably secured to plug 26, thereby permitting pharmaceutical product 100 to pass from first chamber 28 to channel 64 of fluid flow member 62. In this embodiment of the present invention, the opening of pre-pierced channel 42 by plug piercing member 70 is facilitated by contoured exterior surface 102 of plug 26. As depicted in FIG. 4, pre-pierced channel 42 preferably is positioned at a narrowed portion 106 of plug 26, thereby facilitating the outward movement of the walls of plug 26 adjacent pre-pierced channel 42 as plug piercing member 70 is threadably secured to plug 26.

Cap 74 is constructed such that it can be secured to first end portion 58 of syringe body 54, thereby isolating chamber 56 and fluid flow member 62 from an external environment of syringe 52. Cap 74 can be constructed to be secured to syringe body 54 using a variety of known techniques such as threads and interlocking members. Cap 74 preferably is readily removable from syringe body 54 in order to facilitate use of the system of the present invention.

Second end portion 60 of syringe body 54 includes a fluid flow connecting member 76 thereon. Fluid flow connecting member 76 is constructed to connect fluid flow channel 64 of fluid flow member 62 to a fluid delivery system that forms no part of the present invention. The fluid delivery system can be a variety of known systems, including tube sets, cannulas, hypodermic needles, and fluid ports of liquid containers. In the preferred embodiment of the present invention, fluid flow connecting member 76 is configured as a luer that is connectable to mating luers of known construction. The luer can be either a male or female luer, and may include threads based upon the intended use of the system of the present invention.

A second cap 78 is provided to seal fluid flow connecting member 76, thereby isolating fluid flow channel 64 from an external environment of fluid flow connecting member 76. Cap 78 can be constructed to be secured to fluid flow connecting member 76 or to syringe body 54 using a variety of known techniques such as threads and interlocking members. Cap 78 preferably is readily removable from fluid flow connecting member 76 or syringe body 54 in order to facilitate use of the system of the present invention.

In use, ampul 10 is broken open at frangible point 22 as depicted in FIG. 3. Ampul 10 is then placed in connection with syringe 52 as depicted in FIG. 6 such that fluid flow channel 64 is in fluid communication with first chamber 28 of ampul 10. Ampul 10 is then urged into chamber 56 of syringe 52 in a direction indicated by arrows 80, thereby causing plug 26 to move relative to body 12 in an opposite direction indicated by arrows 82, and thereby forcing pharmaceutical product 100 into fluid flow channel 64. Further urging of ampul 10 into chamber 56 of syringe 52 causes pharmaceutical product 100 to flow outwardly from first chamber 28 through fluid flow channel 64 and through fluid flow connecting member 76.

Although the present invention has been described herein with respect to certain preferred embodiments, it will be apparent to one of ordinary skill in the art that various modifications are possible without departing from the intended spirit and scope of the present invention as claimed in the appended claims.

What is claimed is:

1. A pharmaceutical container comprising:
a body defining a chamber therein, said body having a first end portion and a second end portion, said body having a terminal end on said second end portion, and a plug positioned in said chamber defined by said body, said plug spaced from said terminal end, said plug and said body defining a first chamber of said chamber between said plug and said first end portion of said body, said plug and said body defining a second chamber of said chamber between said plug and said terminal end of said second end portion of said body, said plug defining a slit therethrough from said second chamber to said first chamber, said body being frangible at a position on said second end portion between said plug and said terminal end.

2. A pharmaceutical container in accordance with claim 1, wherein said plug is slidably positioned within said chamber defined by said body.

3. A pharmaceutical container in accordance with claim 1, wherein said plug is constructed of a pierceable material.

4. A pharmaceutical container in accordance with claim 1, wherein said body is constructed of glass.

5. A pharmaceutical container in accordance with claim 1, wherein said container further comprises a pharmaceutical product disposed in said first chamber.

6. A pharmaceutical container in accordance with claim 1, wherein said terminal end of said second end portion of said body is substantially flat.

7. A method for packaging a pharmaceutical product, said method comprising the steps of:
providing a container defining a chamber therein, said container having a first end portion and a second end portion, said first end portion being open to an external environment, said container being frangible at a point on said second end portion;

providing a plug constructed to be slidable within said chamber defined by said container, said plug defining a channel therethrough, said channel defined by said plug having threads disposed on a surface thereof;

placing said plug into said chamber defined by said container at a position on a first end portion side of said point at which said container is frangible, said plug and said first end portion of said container defining a first chamber, said plug and said second end portion of said container defining a second chamber;

placing a quantity of a pharmaceutical product in said first chamber; and fluidly sealing said first end portion of said container.

8. A system for delivering a pharmaceutical product, said system comprising:
a pharmaceutical container comprising:
a body defining a chamber therein, said body having a first end portion and a second end portion, said body having a terminal end on said second end portion, and a plug positioned in said chamber defined by said body, said plug spaced from said terminal end, said plug and said body defining a first chamber of said chamber between said plug and said first end portion of said body, said plug and said body defining a second chamber of said chamber between said plug and said terminal end of said second end portion, said body being frangible at a position on said second end portion between said plug and said terminal end, said plug defining a channel therethrough, said channel defined through said plug having threads formed on a wall thereof; and a syringe comprising:
a syringe body defining a chamber therein, said chamber constructed to receive therein said body of said pharmaceutical container, said syringe body having a first open end and a second end opposite said first end; and a fluid flow member mounted within said chamber defined by said syringe body, said fluid flow member defining a fluid flow channel from a first end portion to a second end portion thereof, said first end portion having a means comprising a piercing member constructed to open said channel defined through said plug for establishing fluid contact between said first chamber and said fluid flow channel defined by said fluid flow member, said piercing member having mating threads formed thereon, whereby said piercing member can be threadably advanced into said channel defined through said plug, said second end portion having a means for establishing fluid communication between said fluid flow channel defined by said fluid flow member and an external environment of said syringe body.

9. A system for delivering a pharmaceutical product in accordance with claim 8, wherein said body of said pharmaceutical container is slidable within said syringe body from said first end portion to said second end portion of said syringe body.

10. A system for delivering a pharmaceutical product, said system comprising:

a pharmaceutical container comprising:

a body defining a chamber therein, said body having a first end portion and a second end portion, said body having a terminal end on said second end portion, and a plug positioned in said chamber defined by said body, said plug spaced from said terminal end, said plug and said body defining a first chamber of said chamber between said plug and said first end portion of said body, said plug and said body defining a second chamber of said chamber between said plug and said terminal end of said second end portion, said body being frangible at a position on said second end portion between said plug and said terminal end; and a syringe comprising:

a syringe body defining a chamber therein, said chamber constructed to receive therein said body of said pharmaceutical container, said syringe body having a first open end and a second end opposite said first end; and a fluid flow member mounted within said chamber defined by said syringe body, said fluid flow member defining a fluid flow channel from a first end portion to a second end portion thereof, said first end portion having a means for establishing fluid contact between said first chamber and said fluid flow channel defined by said fluid flow member, said second end portion having a means comprising a luer fitting for establishing fluid communication between said fluid flow channel defined by said fluid flow member and an external environment of said syringe body.

* * * * *